(12) United States Patent
Styczynski et al.

(10) Patent No.: US 7,439,271 B2
(45) Date of Patent: Oct. 21, 2008

(54) REDUCTION OF HAIR GROWTH

(75) Inventors: Peter Styczynski, Wrentham, MA (US); Gurpreet S. Ahluwalia, Potomac, MD (US)

(73) Assignee: The Gillette Company, Boston, MA (US)

( * ) Notice: Subject to any disclaimer, the term of this patent is extended or adjusted under 35 U.S.C. 154(b) by 745 days.

(21) Appl. No.: 09/893,252

(22) Filed: Jun. 27, 2001

(65) Prior Publication Data
US 2003/0012755 A1 Jan. 16, 2003

(51) Int. Cl.
A61K 31/7056 (2006.01)
A01N 43/04 (2006.01)

(52) U.S. Cl. .......................... 514/880; 514/43; 514/44; 514/443

(58) Field of Classification Search ................ 424/70.1, 424/78.02, 401; 524/230.2
See application file for complete search history.

(56) References Cited

U.S. PATENT DOCUMENTS

| | | | |
|---|---|---|---|
| 3,426,137 A | 2/1969 | Philpitt et al. | |
| 4,039,669 A | 8/1977 | Beylar et al. | |
| 4,139,638 A | 2/1979 | Neri et al. | |
| 4,161,540 A | 7/1979 | Neri et al. | |
| 4,191,775 A | 3/1980 | Glen | |
| 4,269,831 A | 5/1981 | Ferrari et al. | |
| 4,370,315 A | 1/1983 | Greff et al. | |
| 4,439,432 A | 3/1984 | Peat | |
| 4,508,714 A | 4/1985 | Cecic et al. | |
| 4,517,175 A | 5/1985 | Iwabuchi et al. | |
| 4,720,489 A * | 1/1988 | Shander ...................... 514/171 | |
| 4,885,289 A | 12/1989 | Breuer et al. | |
| 4,923,862 A * | 5/1990 | Hirota ...................... 514/230.2 | |
| 4,935,231 A | 6/1990 | Pigiet | |
| 5,095,007 A | 3/1992 | Ahluwalia | |
| 5,096,911 A | 3/1992 | Ahluwalia et al. | |
| 5,132,293 A | 7/1992 | Shander et al. | |
| 5,143,925 A | 9/1992 | Shander et al. | |
| 5,189,212 A | 2/1993 | Ruenitz | |
| 5,271,942 A | 12/1993 | Haverhagen | |
| 5,300,284 A | 4/1994 | Wiechers et al. | |
| 5,328,686 A | 7/1994 | Shander et al. | |
| 5,362,748 A | 11/1994 | Schwen et al. | |
| 5,364,885 A | 11/1994 | Ahluwalia et al. | |
| 5,411,991 A | 5/1995 | Shander et al. | |
| 5,444,090 A | 8/1995 | Ahluwalia et al. | |
| 5,455,234 A | 10/1995 | Ahluwalia et al. | |
| 5,468,476 A | 11/1995 | Ahluwalia et al. | |
| 5,474,763 A | 12/1995 | Shander et al. | |
| 5,554,608 A | 9/1996 | Ahluwalia et al. | |
| 5,645,825 A | 7/1997 | Hillebrand et al. | |
| 5,648,394 A | 7/1997 | Boxall et al. | |
| 5,652,273 A | 7/1997 | Henry et al. | |
| 5,674,477 A | 10/1997 | Ahluwalia | |
| 5,728,736 A | 3/1998 | Shander et al. | |
| 5,776,442 A | 7/1998 | Ahluwalia | |
| 5,824,665 A | 10/1998 | Henry et al. | |
| 5,840,752 A | 11/1998 | Henry et al. | |
| 5,908,867 A | 6/1999 | Henry et al. | |
| 5,939,458 A | 8/1999 | Henry et al. | |
| 5,958,946 A | 9/1999 | Styczynski et al. | |
| 5,962,466 A | 10/1999 | Styczynski et al. | |
| 6,017,912 A | 1/2000 | Bussell | |
| 6,020,006 A | 2/2000 | Styczynski et al. | |
| 6,037,326 A | 3/2000 | Styczynski et al. | |
| 6,060,471 A | 5/2000 | Styczynski et al. | |
| 6,093,748 A | 7/2000 | Ahluwalia et al. | |
| 6,110,458 A * | 8/2000 | Freeman et al. .......... 424/93.21 | |
| 6,121,269 A | 9/2000 | Henry et al. | |
| 6,218,435 B1 | 4/2001 | Henry et al. | |
| 6,235,737 B1 | 5/2001 | Styczynski et al. | |
| 6,239,170 B1 | 5/2001 | Alhuwalia et al. | |
| 6,248,751 B1 | 6/2001 | Alhuwalia et al. | |
| 6,299,865 B1 | 10/2001 | Styczynski et al. | |
| 6,368,789 B1 * | 4/2002 | West et al. ...................... 435/6 | |
| 6,479,466 B1 * | 11/2002 | Redfield et al. ................ 514/45 | |
| 6,702,705 B1 * | 3/2004 | von Borstel et al. ....... 435/188.5 | |
| 6,713,251 B2 * | 3/2004 | Stuyver et al. .................. 435/5 | |

FOREIGN PATENT DOCUMENTS

| | | |
|---|---|---|
| EP | 0 413 528 B1 | 2/1991 |
| EP | 0 532 219 A2 | 3/1993 |
| GB | 1 458 349 | 12/1976 |
| JP | 9-113096 | 6/1997 |
| WO | WO 98/02134 | 1/1998 |
| WO | WO 98/23276 | 6/1998 |
| WO | WO 99/19466 | 4/1999 |

OTHER PUBLICATIONS

Ueno et al., Biochemistry 39: 5995-6002, 2000, Inhibition of human telomerase by rubromycins: implication of spiroketal system of the compounds as an active moiety.

Kitagawa et al., "Demethylating Reagent 5-Azacytidine Inhibits Telomerase Activity in Human Prostate Cancer Cells through Transcriptional Repression of $h$TERT", Clin. Cancer Res. 6: 2868-2875, Jul. 2000.

Caprio et al., A Novel Inhibitor of Human Telomerase Derived from 10$H$indolo[3,2-b]quinoline, Bioorg. Med. Chem. Letters, vol. 10, pp. 2063-2066, 2000.

Szatmari et al., "Modified Telomeric Repeat Amplification Protocol: A Quantitative Radioactive Assay for Telomerase without Using Electrophoresis", Analytical Biochemistry, vol. 282, pp. 80-88, 2000.

Krupp et al., "Cell proliferation, carcinogenesis and diverse mechanisms of telomerase regulation", CMLS, Cell. Mol. Life Sci., vol. 57, pp. 464-486, 2000.

Murakami et al., "Inhibition of Telomerase Activity and Cell Proliferation by a Reverse Transcriptase Inhibitor in Gynaecological Cancer Cell Lines", European Journal of Cancer, vol. 35, No. 6, pp. 1027-1034, 1999.

Naasani et al., "FJ5002: A Potent Telomerase Inhibitor Identified by Exploiting the Disease-oriented Screening Program with COMPARE Analysis", Cancer Research, vol. 59, pp. 4004-4011, Aug. 15, 1999.

(Continued)

*Primary Examiner*—Sreeni Padmanabhan
*Assistant Examiner*—Gina Yu
(74) *Attorney, Agent, or Firm*—Fish & Richardson P.C.

(57) ABSTRACT

Mammalian hair growth is reduced by applying an inhibitor of telomerase to the skin.

52 Claims, No Drawings

OTHER PUBLICATIONS

Lee et al., "Improved Inhibitors of Glucosylceramide Synthase", J. Biol. Chem., vol. 274, pp. 14662-14669, May 21, 1999.

Spinedi et al., "N-Oleoylethanolamine Inhibits Glucosylation of Natural Ceramides in CHP-100 Neuroepithelioma Cells: Possible Implications for Apoptosis", Biochemical and Biophysical Research Comm., pp. 456-459 (1999), vol. 255.

Beltz et al., "The Effects of Telomerase Inhibitors on Lymphocyte Function", Anticancer Res. 19: 3205-3211, 1999.

Hayakawa et al., "Isothiazolone Derivatives Selectively Inhibit Telomerase from Human and Rat Cancer Cells in Vitro", Biochemistry 38: 11501-11507, 1999.

Narisawa et al., "Inhibitory Effects of Ursodeoxycholic Acid on N-Methyl-nitrosourea-Induced Colon Carinogenesis and Colonic Mucosal Telomerase Activity in F344 Rats", J. Exp. Clin. Cancer Res. 18: 259-266, 1999.

Tabata et al., "Diazaphilonic Acid, a New Azaphilone with Telomerase Inhibitory Activity", J. Antibiot. 52: 412-414, 1999.

Herbert et al., "Inhibition of human teleomerase in immortal human cells leads to progressive telomere shortening and cell death", Proced. Natl. Acad. Sci. vol. 96, 14276-14281, Dec. 7, 1999.

Han et al., "Accelerated Assembly of G-Quadruplex Structures by a Small Molecule", Biochemistry 38: 6981, 1999.

Page et al., "The Cytotoxic Effects of Single-Stranded Telomere Mimics on OMA-BL1 Cells", Exp. Cell Res. 252: 41, 1999.

Harrison et al., "Human Telomerase Inhibition by Substituted Acridine Derivatives", Bioorg. Med Chem. Lett. 9: 2463, 1999.

Izbicka et al., "Effects of Cationic Porphyrins as G-Quadruplex Interactive Agents in Human Tumor Cells", Cancer Res. 59: 639, 1999.

Bednarek et al., "Suppression of cell proliferation and telomerase activity in 4-(hydroxyphenyl)retinamide-treated mammary tumors", Carcinogenesis, vol. 20, No. 5, pp. 879-883, 1999.

Ogoshi et al., "In Situ Hybridization Analysis of the Expression of Human Telomerase RNA in Normal and Pathologic Conditions of the Skin", The Journal of Investigative Dermatology, vol. 110, No. 5, May 1998.

Botchkarev et al., "A New Role for Neurotrophin-3 Involvement in the Regulation of Hair Follicle Regression (Catagen)", American Journal of Pathology, vol. 153, No. 3, Sep. 1998.

Botchkarev et al., "Neurotrophin-3 Involvement in the Regulation of Hair Follicle Morphogenesis", The Journal of Investigative Dermatology, vol. 111, No. 2, Aug. 1998.

Ichikawa et al., "Glucosylceramide synthase and glycosphingolipid synthesis", trends in Cell Biology, pp. 198-202, May 1998.

Glukhov et al., "Inhibition of Telomerase Activity of Melanoma Cells in Vitro by Antisense Oligonucleotides", Biochem. Biophys Res. Comm. 248: 368-371, 1998.

Togashi et al., "Inhibition of Human Telomerase Activity by Alterperylenol", Oncol. Res. 10: 449-453, 1998.

Perry et al., "1,4- and 2,6-Disubstituted Amidoanthracene-9,10-dione Derivatives as Inhibitors of Human Telomerase", J. Med. Chem. 41: 41: 3253-3260, 1998.

Fedoroff et al., "NMR-Based Model of a Telomerase-Inhibiting Compound Bound to G-Quadruplex DNA". American Chemical Society, vol. 37, No. 36, pp. 12367-12374, Sep. 8, 1998.

Wheelhouse et al., "Cationic Porophyrins as Telomerase Inhibitors: the Interaction of Tetra-(N-methyl-4-pyridyl)porphine with Quadruplex DNA", J. Am. Chem Soc. vol. 120, No. 13, pp. 3261-3262, 1998.

Hoffman et al., "Interleukin-1-β-Induced Inhibition of Hair Growth In Vitro is Mediated by Cyclic AMP", The Journal of Investigative Dermatology, vol. 108, pp. 40-42, 1997.

Yamakuchi et al., "New Quinolones, ofloxacin and levofloxacin, Inhibit Telomerase Activity in Transitional Cell Carcinoma Cell Lines", Cancer Letters, 119: 213-219, 1997.

Yegorov et al., "Blockade of Telomerase Function by Necleoside Analogs", Biochemistry vol. 62: 1296-1305, 1997.

Kohtaro et al., "Telomerase Activity in Human Leukemic Cell Lines is Inhibited by Antisense Pentadecadeoxynucleotides Targeted Against c-myc mRNA", Biochem. Biophys. Res. Comm. 241: 775-781, 1997.

Sun et al., "Inhibition of Human Telomerase by a G-Quadruplex Interactive Compound", J. Med Chem. 40: 2113, 1997.

Mata et al., "A Hexameric Phosphorothioate Oligonucleotide Telomerase Inhibitor Arrests Growth of Burkitt's Lymphoma Cells in Vitro and in Vivo", Toxicol. Appl. Pharmacol. 144: 189, 1997.

Fujimoto et al., "Telomerase Activity in Human Leukemic Cell Lines is Inhibited by Antisense Pentadecadeoxynucleotides Targeted Against c-myc mRNA", Biochemical and Biophysical Research Communications, 241, 775-781 (1997).

Ramirez et al., "Telomerase Activity Concentrates in the Mitotically Active Segments of Human Hair Follicles", The Journal of Investigative Dermatology, vol. 108, No. 1, Jan. 1997.

Bielawska et al., "(1S,2R)-D-erythro-2-(N-Myrisoylamino)-1-phenyl-1-propanol as an Inhibitor of Ceramidase", The Journal of Biological Chemistry, vol. 271, pp. 12646-12654, May 24, 1996.

Rani et al., "Cell Cycle Arrest Induced by an Inhibitor of Glucosylceramide Synthase", The American Society for Biochemistry and Molecular Biology, Inc., vol. 270, pp. 2859-2867, Feb. 10, 1995.

Blasco, M.A., "Functional Characterization and Dvelopmental Regulation of Mouse Telomerase RNA", Science 269: 1267, 1995.

Platt et al., "N-Butyldeoxynojirimycin Is a Novel Inhibitor of Glycolipid Biosynthesis", The Journal of Biological Chemistry, vol. 269, pp. 8362-8365, Mar. 18, 1994.

Andrew G. Messenger, "The Control of Hair Growth: An Overview", The Society for Investigative Dermatology, Inc., 1993.

Weinberg et al., "Reconstitution of Hair Follicle Development In Vivo: Determination of Follicle Formation, Hair Growth, and Hair Quality by Dermal Cells", The J. of Invest. Dermatology, vol. 100, No. 3, Mar. 1993.

Matsuo et al., "A rapid and simple assay method for UDP-glucose:ceramide glucosyltransferase", Biochemicsa et al., Biophysica Acta, pp. 97-103 (1992).

Ebling et al., "The Biology of Hair", Dermatologic Clinics, vol. 5, pp. 467-481, Jul. 1987.

Hattori et al., "Biochemical Analysis of Hair Growth from the Aspects of Aging and Enzyme Activities", The Journal of Dermatology, vol. 10, 1983.

Yoshio Sato, "The Hair Cycle and Its Control Mechanism", Biology and Disease of Hair, pp. 3-13, 1975.

Adachi et al., "Human Hair Follicles: Metabolism and Control Mechanisms", Journal of the Society of Cosmetic Chemists, 21, 901-924, Dec. 9, 1970.

* cited by examiner

SEQUENCE LISTING

```
<160> NUMBER OF SEQ ID NOS: 4

<210> SEQ ID NO 1
<211> LENGTH: 18
<212> TYPE: DNA
<213> ORGANISM: Homo sapiens

<400> SEQUENCE: 1
ttagggttag ggttaggg                                                 18

<210> SEQ ID NO 2
<211> LENGTH: 15
<212> TYPE: DNA
<213> ORGANISM: Homo sapiens

<400> SEQUENCE: 2
acgttgaggg gcatc                                                    15

<210> SEQ ID NO 3
<211> LENGTH: 18
<212> TYPE: DNA
<213> ORGANISM: Homo sapiens

<400> SEQUENCE: 3
atgaaaatca gggttagg                                                 18

<210> SEQ ID NO 4
```

```
-continued

<211> LENGTH: 13
<212> TYPE: RNA
<213> ORGANISM: Homo sapiens

<400> SEQUENCE: 4
caguuagggu uag                                                          13
```

REDUCTION OF HAIR GROWTH

BACKGROUND

The invention relates to reducing hair growth in mammals, particularly for cosmetic purposes.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; and Shander et al., U.S. Pat. No. 5,132,293.

Telomerase is an enzyme that is responsible for catalyzing the addition of simple hexameric nucleotide sequences on the ends of linear chromosomal DNA. The ends including these sequences generally are known as "telomeric DNA." Telomeric DNA typically is up to 200 base pairs long in humans. The maintenance of telomeric DNA by telomerase protects the cell from exonucleocytic degradation and subsequent cell senescence. With each cell replication telomeric DNA, which consists not of blunt-ended double stranded DNA but rather of a 3' single stranded G-rich protruding overhang, shortens and, once reaching a critical threshold, triggers the cell to senesce as a sort of checkpoint control. It has been postulated that this mechanism may represent a biological clock controlling the lifespan of the cell. To compensate for the loss of telomeric DNA during cell replication, cells express the enzyme telomerase, a ribonucleoprotein, which includes an RNA component that serves as a template for the synthesis of telomeric DNA. Certain cell types express high levels of telomerase. These include some tumor cells, cells of renewal tissues (e.g., skin, intestine, blood), and some immortalized cells with high proliferative capacity. Investigators have shown that telomerase is present in blood progenitor cells and activated lymphocytes, epidermis and intestine. Recent findings have shown that peripheral blood lymphocytes are "telomerase competent" such that if they are not dividing or quiescent they are telomerase negative and, when they are mitogenically activated and become proliferative, they are telomerase positive. Quiescent cells are always telomerase negative and cell proliferation is a prerequisite for telomerase activation in telomerase competent cells. It is possible that high telomerase levels reflect either a fraction of proliferating cells or markedly elevated telomerase activity in the individual cells.

SUMMARY

In one aspect, the invention provides a method (typically a cosmetic method) of reducing unwanted mammalian (preferably human) hair growth, for example, androgen-stimulated hair growth, by applying to the skin an inhibitor of telomerase in an amount effective to reduce hair growth. The unwanted hair growth may be undesirable from a cosmetic standpoint or may result, for example, from a disease or an abnormal condition (e.g., hirsutism). In another aspect, the invention provides a method of reducing unwanted mammalian hair growth by applying to the skin a compound that reduces telomerase levels in hair follicles. In another aspect, the invention provides a method of reducing unwanted mammalian hair growth by applying to the skin a compound that reduces telomerase mRNA expression. In a further aspect, the invention provides a method of reducing unwanted mammalian hair growth by applying to the skin a compound that promotes the erosion of telomeric DNA.

Typically, in practicing the aforementioned methods, the inhibitor or compound will be included in a topical composition along with a dermatologically or cosmetically acceptable vehicle. Accordingly, the present invention also relates to topical compositions comprising a dermatologically or cosmetically acceptable vehicle and an inhibitor of telomerase in an amount effective to reduce hair growth. The present invention further relates to topical compositions comprising a dermatologically or cosmetically acceptable vehicle and (a) a compound that reduces telomerase levels in hair follicles or (b) a compound that reduces telomeric mRNA expression in hair follicles or (c) a compound that promotes erosion of telomeric DNA in hair follicles, wherein the compound is present in an amount effective to reduce hair growth.

In addition, the present invention relates to the use of an inhibitor of telomerase for the manufacture of a therapeutic topical composition for reducing hair growth. Further, the present invention relates to the use of a compound for the manufacture of a therapeutic topical composition for reducing hair growth wherein the compound is (a) a compound that reduces telomerase levels in hair follicles or (b) a compound that reduces telomeric mRNA expression in hair follicles or (c) a compound that promotes erosion of telomeric DNA in hair follicles.

Other features and advantages of the invention may be apparent from the description of the preferred embodiments thereof, and from the claims.

DETAILED DESCRIPTION

An example of a preferred composition includes at least one inhibitor of telomerase in a cosmetically and/or dermatologically acceptable vehicle. The composition may be a solid, semi-solid, or liquid. The composition may be, for example, a cosmetic and dermatologic product in the form of an, for example, ointment, lotion, foam, cream, gel, or solution. The composition may also be in the form of a shaving preparation or an aftershave. The vehicle itself can be inert or it can possess cosmetic, physiological and/or pharmaceutical benefits of its own.

Examples of inhibitors of telomerase include a class of quinone antibiotics, rubromycins and purpuromycins and their analogs (Ueno et al. *Biochemistry* 39: 5995-6002, 2000); 3'-deoxy-2:3'-didehydrothymidine, dideoxyinosine (Beltz et al. *Anticancer Res.* 19: 3205-3211, 1999); the oligonucleotide sequence that mimics telomeric DNA (TTAGGG)$_3$ (SEQ ID NO:1) (Glukhov et al. *Biochem. Biophys. Res. Comm.* 248: 368-371, 1998); levofloxacin and ofloxacin (Yamakuchi et al. *Cancer Lett.* 119: 213-219, 1997); carbovir, azidothymidine (AZT) (Yegorov et al. *Biochemistry* 62: 1296-1305, 1997); antisense nucleotides against c-myc mRNA including ACGTTGAGGGGCATC (SEQ ID NO:2)(Kohtaro and Takahashi, *Biochem. Biophys. Res. Comm.* 241: 775-781, 1997); isothiazolone derivatives such as 2-[3-(trifluoromethyl)phenyl]isothiazolin-3-one (Hayakawa et al. *Biochemistry* 38: 11501-11507, 1999); ursodeoxycholic acid (Narisawa et al. *J. Exp. Clin. Cancer Res.* 18: 259-266, 1999); diazaphilonic acid (Tabata et al. *J. Antibiot.* 52: 412-414, 1999); the fungal metabolite, alterperylenol (Togashi et al. *Oncol. Res.* 10: 449-453, 1998); regioisomeric difunctionalized amidoanthracene-9,10-diones substituted at the 1,5-, 1,8-, and 2,7-positions (Perry et al. *J. Med. Chem.* 41: 4873-4884, 1998); 5-azacytidine (Kitagawa et al. *Clin. Cancer Res.* 6: 2868-2875, 2000); 3,4,9,10-perylenetetracarboxylic diimide-based ligands ((Fedoroff et al., *Biochem.* 37: 12367-12374, 1998); 10H-indolo[3,2-b]quinoline (Caprio et al. *Bioorg. Med. Chem. Lett.* 10: 2063-2066, 2000); 2'-O-MeRNA telomerase oligomers, 2'-O-alkylRNA telomerase oligomers, fomivirsen (Herbert et al. *Proced. Natl. Acad. Sci. USA* 96: 14276-14281, 1999); cationic porphryins (Wheelhouse et al. *J. Am. Chem Soc.* 120: 3261-3262, 1998); diazaphilonic acid (Tabata et al. *J. Antibiot.* 52: 412-412, 1999); telomerase inhibitor I (2,6-bis[3-(2-hydroxymethyl)-N-methylpiperidino]propionamido]-anthracene-9,10-dione, diiodide) (Sun et al. *J. Med Chem.* 40: 2113, 1997); telomerase inhibitor II (5'-d(ATGAAAAT-CAGGGTTAGG)-3';SEQ ID NO:3) (Blasco, M. A., *Science* 269: 1267, 1995); telomerase inhibitor III (5'-d(TTAGGG)-3') (Mata et al., *Toxicol. Appl. Pharmacol.* 144: 189, 1997); telomerase inhibitor IV (PIPER or N,N'-bis[2-(1-piperidino)ethyl]-3,4,9,10-perylenetetracarboxylic diimide) (Han et al. *Biochemistry* 38: 6981, 1999); telomerase inhibitor V (BSU-1051 or 2,6-bis[3-(N-piperidino)propionamido]anthracene-9,10-dione) (Perry et al. *J. Med Chem.* 41: 3253, 1998); telomerase inhibitor VI (5'-CAGUUAGGGUUAG-3'; (SEQ ID NO:4) ) (Herbert et al. *Proc. Natl. Acad. Sci. USA* 96: 14276, 1999); telomerase inhibitor VII (5'-d(GGG~GGG)-3') (Page et al. *Exp. Cell Res.* 252: 41, 1999); telomerase inhibitor VIII (3,6-bis(3-piperidinopropionamido)-acridine) (Harrison et al. *Bioorg. Med Chem. Lett.* 9: 2463, 1999); and TMPyP4 (meso-5,10,15,20-tetrakis-(N-methyl-4-pyridy) porphine)(Izbicka et al. *Cancer Res.* 59: 639, 1999).

The inhibitor inhibits the catalytic action of telomerase, for example, by acting on telomerase itself or by acting on the substrate targeted by telomerase. A specific chemical name for a substance also encompasses pharmaceutically acceptable salts of the substance.

The composition may include more than one inhibitor of telomerase activity. In addition, the composition may include one or more other types of hair growth reducing agents, such as those described in U.S. Pat. Nos. 4,885,289; 4,720,489; 5,132,293; 5,096,911; 5,095,007; 5,143,925; 5,328,686; 5,440,090; 5,364,885; 5,411,991; 5,648,394; 5,468,476; 5,475,763; 5,554,608; 5,674,477; 5,728,736; 5,652,273; WO 94/27586; WO 94/27563; and WO 98/03149, all of which are incorporated herein by reference.

The concentration of the inhibitor in the composition may be varied over a wide range up to a saturated solution, preferably from 0.1% to 30% by weight or even more; the reduction of hair growth increases as the amount of compound applied increases per unit area of skin. The maximum amount effectively applied is limited only by the rate at which the inhibitor penetrates the skin. The effective amounts may range, for example, from 10 to 3000 micrograms or more per square centimeter of skin.

The vehicle can be inert or can possess cosmetic, physiological and/or pharmaceutical benefits of its own. Vehicles can be formulated with liquid or solid emollients, solvents, thickeners, humectants and/or powders. Emollients include stearyl alcohol, mink oil, cetyl alcohol, oleyl alcohol, isopropyl laurate, polyethylene glycol, olive oil, petroleum jelly, palmitic acid, oleic acid, and myristyl myristate. Solvents include ethyl alcohol, isopropanol, acetone, diethylene glycol, ethylene glycol, dimethyl sulfoxide, and dimethyl formamide.

The composition also can include components that enhance the penetration of the inhibitor into the skin and/or to the site of action. Examples of penetration enhancers include urea, polyoxyethylene ethers (e.g., Brij-30 and Laureth-4), 3-hydroxy-3,7,11-trimethyl-1,6,10-dodecatriene, terpenes, cis-fatty acids (e.g., oleic acid, palmitoleic acid), acetone, laurocapram, dimethylsulfoxide, 2-pyrrolidone, oleyl alcohol, glyceryl-3-stearate, propan-2-ol, myristic acid isopropyl ester, cholesterol, and propylene glycol. A penetration enhancer can be added, for example, at concentrations of 0.1% to 20% or 0.5% to 5% by weight.

The composition also can be formulated to provide a reservoir within or on the surface of the skin to provide for a continual slow release of the inhibitor. The composition also may be formulated to evaporate slowly from the skin, allowing the inhibitor extra time to penetrate the skin.

The following are examples of compositions including a compound that inhibits telomerase.

EXAMPLE 1

A composition prepared containing up to 10% by weight of AZT, ofloxacin or TMPyP4 in a vehicle containing water 68%, ethanol 16%, propylene glycol 5%, dipropylene glycol 5%, benzyl alcohol 4% and propylene carbonate 2%.

EXAMPLE 2

A composition containing up to 2.5% by weight of telomerase inhibitor Type I, telomerase inhibitor Type IV or telomerase inhibitor Type V in a vehicle containing water 68%, ethanol 16%, propylene glycol 5%, dipropylene glycol 5%, benzyl alcohol 4% and propylene carbonate 2%.

EXAMPLE 3

A composition containing active compounds in Example 1 in a vehicle containing water 80.84%, glyceryl stearate 4.24%, polyethylene glycol 100-stearate 4.09%, cetearyl alcohol 3.05%, ceteareth-20 2.5%, mineral oil 2.22%, stearyl alcohol 1.67%, dimethicone 0.56%.

EXAMPLE 4

A composition containing active compounds in Example 2 in a vehicle containing water 80.84%, glyceryl stearate 4.24%, polyethylene glycol 100-stearate 4.09%, cetearyl alcohol 3.05%, ceteareth-20 2.5%, mineral oil 2.22%, stearyl alcohol 1.67%, dimethicone 0.56%.

EXAMPLE 5

Any one or more of the previous examples in combination with one or more of the penetration enhancers selected from: urea, polyoxyethylene-4-lauryl ether, 3-hydroxy-3,7,11-trimethyl-1,6,10-dodecatriene (nerolidol) and/or cis-9-octadecanoic acid (oleic acid).

The composition should be topically applied to a selected area of the body from which it is desired to reduce hair growth. For example, the composition can be applied to the face, particularly to the beard area of the face, i.e., the cheek, neck, upper lip, and chin. The composition also may be used as an adjunct to other methods of hair removal including shaving, waxing, mechanical epilation, chemical depilation, electrolysis and laser-assisted hair removal.

The composition can also be applied to the legs, arms, torso or armpits. The composition is particularly suitable for reducing the growth of unwanted hair in women having hirsutism or other conditions. In humans, the composition should be applied once or twice a day, or even more frequently, to achieve a perceived reduction in hair growth. Perception of reduced hair growth could occur as early as 24 hours or 48 hours (for instance, between normal shaving intervals) following use or could take up to, for example, three months. Reduction in hair growth is demonstrated when, for example, the rate of hair growth is slowed, the need for removal is reduced, the subject perceives less hair on the treated site, or quantitatively, when the weight of hair removed (i.e., hair mass) is reduced.

Golden Syrian Hamster Assay

Male intact Golden Syrian hamsters are considered acceptable models for human beard hair growth in that they display oval shaped flank organs, one on each side, each about 8 mm. in major diameter. These organs produce fine light colored hair typical of the animal pelage found on the body. In response to androgens the flank organs produce dark coarse hair similar to male human beard hair. To evaluate the effectiveness of a composition in reducing hair growth, the flank organs of each of a group of hamsters are depilated by applying a thioglycolate based chemical depilatory (Surgex) and/or shaved. To one organ of each animal 10 µl. of vehicle alone once a day is applied, while to the other organ of each animal an equal amount of vehicle containing the compound under evaluation is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide a reduction in hair growth of at least about 15% and more preferably at least about 20%, when tested in the Golden Syrian hamster assay. Compositions described in Example 1 (above) were tested in the Golden Syrian hamster assay. Inhibition of flank organ hair growth was demonstrated following the topical administration of the composition. While the mechanism of ofloxacin inhibition of telomerase is not understood, TMPyP4 apparently inhibits telomerase by binding to and stabilizing the DNA quadruplex structure, which forms after at least two rounds of telomeric extension, resulting in inhibition of telomerase. AZT, a well-characterized inhibitor of reverse transcriptase, inhibits telomerase by blocking the transcription function of the enzyme. The results of the assay are shown in Table I:

TABLE I

Effect of Inhibitors of Telomerase on Hair Mass Reduction

| Compound | Dose | Left (mg)[1] | Right (mg)[2] | % Inhibition |
|---|---|---|---|---|
| AZT | 10% | 2.10 ± .18 | 2.72 ± .20 | 22 ± 7 |
| Ofloxacin | 5% | 1.56 ± .24 | 2.72 ± .47 | 39 ± 7 |
| TMPyP4 | 1% | 1.73 ± .23 | 2.37 ± .19 | 28 ± 8 |

[1]Left hair mass for vehicle with test compound.
[2]Right hair vehicle mass control.

Human Hair Follicle Growth Assay

Tissue source—Human skin was obtained from a plastic surgeon as a by-product of face-lift procedures. Immediately after removal, the skin was placed in Williams E medium containing antibiotics and refrigerated. The Williams E medium is a commercially obtained medium which has been formulated with essential nutrients for maintaining viability of tissues or cells such as of hair follicle in an in-vitro environment.

Hair Follicle Isolation and Culture—Human hair follicles in growth phase (anagen) were isolated from face-lift tissue under a dissecting scope using a scalpel and watchmakers forceps. The skin was sliced into thin strips exposing 2-3 rows of follicles that could readily be dissected. Follicles were placed into 0.5 ml Williams E medium supplemented with 2 mM L-glutamine, 10 µg/ml insulin, 100 ng/ml hydrocortisone, 100 units penicillin, 0.1 mg/ml streptomycin and 0.25 µg/ml amphotericin B. The follicles were incubated in 24 well plates (1 follicle/well) at 37° C. in an atmosphere of 5% $CO_2$ and 95% air. Hair follicles were videorecorded in the 24-well plates under the dissecting scope under a power of 20×. Typically, hair follicle lengths were measured on day 0 (day follicles were placed in culture) and again on day 7. When testing compounds, the compound was included in the culture medium from time 0 and remained in the medium throughout the course of the experiment.

In this system follicle cells differentiate to form hair fiber and increase in length at a rate not dissimilar from that of humans, in vivo. Typically, hair fiber from these in-vitro follicles grow about 0.3 mm/day. Growth has been shown to occur for as long as 10 to 14 days. This model of human hair growth is capable of identifying inhibitors of hair growth. The selective telomerase inhibitors -I, -IV and -V were obtained from Calbiochem, La Jolla, Calif. The data in Tables II-VI below show dose-dependent inhibition of human hair follicle growth by various compounds.

TABLE II

Inhibition of Human Hair Growth by Inhibitors of Telomerase

| Compound | Dose | Length Increase (mm) | % Inhibition |
|---|---|---|---|
| Ofloxacin | 100 µM | 1.16 ± .12 | 31 ± 7 |
| TMPyP4 | 73 µM | .468 ± .09 | 52 ± 9 |

Control hair follicle growth was 1.67 ± .10 for the ofloxacin group and 0.984 ± .11 for the TMPyP4 group. Hair growth was determined by subtracting total hair follicle length on day 0 from total hair follicle length on day 6. % Inhibition = hair growth for inhibitor treated follicles/hair growth for control × 100.

TABLE III

Inhibition of Human Hair Growth by Telomerase Inhibitor I

| Compound | Dose | Length Increase (mm) | % Inhibition |
|---|---|---|---|
| Control | — | 1.79 ± .09 | 0 ± 8 |
| Telomerase Inhibitor I* | 10 µM | 1.18 ± .10 | 34 ± 6 |
| Telomerase Inhibitor I* | 100 µM | .286 ± .09 | 84 ± 5 |

*Telomerase inhibitor I: 2,6-bis[3-(2-hydroxymethyl)-N-methylpiperidino] propion-amido]-antbracene-9,10-dione, diiodide. Hair growth was determined by subtracting total hair follicle length on day 0 from total hair follicle length on day 6. % Inhibition = hair growth for inhibitor treated follicles/hair growth for control × 100.

TABLE IV

Inhibition of Human Hair Growth by Telomerase Inhibitor IV

| Compound | Dose | Length Increase (mm) | % Inhibition |
|---|---|---|---|
| Control | — | 1.54 ± .14 | 0 ± 9 |
| Telomerase Inhibitor IV* | 10 µM | 1.39 ± .16 | 10 ± 10 |
| Telomerase Inhibitor IV* | 100 µM | 0.80 ± .12 | 48 ± 8 |

*Telomerase inhibitor IV: N,N'-bis[2-(1-piperidino)ethyl]-3,4,9,10-perylene-tetracarboxylic diimide. Hair growth was determined by subtracting total hair follicle length on day 0 from total hair follicle length on day 6. % Inhibition = 1-(hair growth for inhibitor treated follicles/hair growth for control) × 100.

TABLE V

Inhibition of Human Hair Growth by Telomerase Inhibitor V

| Compound | Dose | Length Increase (mm) | % Inhibition |
|---|---|---|---|
| Control | — | 1.54 ± .14 | 0 ± 9 |
| Telomerase Inhibitor V* | 10 µM | 1.32 ± .13 | 14 ± 8 |
| Telomerase Inhibitor V* | 100 µM | 0.25 ± .30 | 68 ± 19 |

*Telomerase inhibitor V: 2,6-bis[3-(N-piperidino)propionamido]-antbracene-9,10-dione. Hair growth was determined by subtracting total hair follicle length on day 0 from total hair follicle length on day 6. % Inhibition = hair growth for inhibitor treated follicles/hair growth for control × 100.

TABLE VI

Inhibition of Human Hair Growth by Ofloxacin

| Compound | Dose | Length Increase (mm) | % Inhibition |
|---|---|---|---|
| Control* | — | 1.67 ± .10 | 0 ± 8 |
| Ofloxacin | 0.01 µM | 1.51 ± .24 | 10 ± 14 |
| Ofloxacin | 0.1 µM | 1.16 ± .12 | 30 ± 7 |
| Ofloxacin | 1.0 µM | 0.43 ± .11* | 69 ± 8 |

*Control hair follicle growth for the 1 mM ofloxacin experiment was 1.40 ± .17 mm. Hair growth was determined by subtracting total hair follicle length on day 0 from total hair follicle length on day 6. % Inhibition = hair growth for inhibitor treated follicles/hair growth for control × 100.

Taken together these data indicate that inhibition of telomerase in hair follicles is an effective means of reducing or inhibiting the rate of hair growth. It also follows that blocking the expression of telomerase protein levels or any alteration that reduces the hair follicles ability to maintain its telomeric DNA will also result in the inhibition of hair growth.

Other embodiments are within the claims.

What is claimed is:

1. A method of reducing mammalian hair growth which comprises selecting an area of skin on a mammal from which reduced hair growth is desired; and applying to said area of skin a dermatologically acceptable composition comprising an inhibitor of telomerase in an amount effective to reduce hair growth.

2. The method of claim 1, wherein said inhibitor is ofloxacin.

3. The method of claim 1, wherein said inhibitor is TMPyP4.

4. The method of claim 1, wherein said inhibitor is telomerase inhibitor I.

5. The method of claim 1, wherein said inhibitor is telomerase inhibitor IV.

6. The method of claim 1, wherein said inhibitor is telomerase inhibitor V.

7. The method of claim 1, wherein said inhibitor is AZT.

8. The method of claim 1, wherein said inhibitor is a rubromycin.

9. The method of claim 1, wherein said inhibitor is a purpuromycin.

10. The method of claim 1, wherein said inhibitor is 3'-deoxy-2:3'-didehydrothymidine.

11. The method of claim 1, wherein said inhibitor is dideoxyinosine.

12. The method of claim 1, wherein said inhibitor is (TTAGGG)3.

13. The method of claim 1, wherein said inhibitor is levofloxacin.

14. The method of claim 1, wherein said inhibitor is carbovir.

15. The method of claim 1, wherein said inhibitor is ACGTTGAGGGGCATC.

16. The method of claim 1, wherein said inhibitor is 2-[3-(trifluoromethyl)phenyl]isothiazolin-3-one.

17. The method of claim 1, wherein said inhibitor is ursodeoxycholic acid.

18. The method of claim 1, wherein said inhibitor is diazaphilonic acid.

19. The method of claim 1, wherein said inhibitor is alterperylenol.

20. The method of claim 1, wherein said inhibitor is 5-azacytidine.

21. The method of claim 1, wherein said inhibitor is a 3,4,9,10-perylenetetracarboxylic diimide-based ligand.

22. The method of claim 1, wherein said inhibitor is 10H-indolo[3,2-b]quinoline.

23. The method of claim 1, wherein said inhibitor is a 2'-O-MeRNA telomerase oligomer.

24. The method of claim 1, wherein said inhibitor is a 2'-O-alkyl RNA telomerase oligomer.

25. The method of claim 1, wherein said inhibitor is fomivirsen.

26. The method of claim 1, wherein said inhibitor is a cationic porphryin.

27. The method of claim 1, wherein said inhibitor is diazaphilonic acid.

28. The method of claim 1, wherein said inhibitor is telomerase inhibitor II.

29. The method of claim 1, wherein said inhibitor is telomerase inhibitor III.

30. The method of claim 1, wherein said inhibitor is telomerase inhibitor VI.

31. The method of claim 1, wherein said inhibitor is telomerase inhibitor VII.

32. The method of claim 1, wherein said inhibitor is telomerase inhibitor VIII.

33. The method of claim 1, wherein the concentration of said inhibitor in said composition is between 0.1% and 30% by weight of the composition.

34. The method of claim 1, wherein the composition provides a reduction in hair growth of at least 20% when tested in the Golden Syrian Hamster assay.

35. The method of claim 1, wherein the composition provides a reduction in hair growth of at least 15% when tested in the Golden Syrian Hamster assay.

36. The method of claim 1, wherein the inhibitor is applied to the skin in an amount of from 10 to 3000 micrograms of said compound per square centimeter of skin.

37. The method of claim 1, wherein said mammal is a human.

38. The method of claim 36, wherein said area of skin is on the face of a human.

39. The method of claim 37, wherein the composition is applied to the area of skin in conjunction with shaving.

40. The method of claim 37, wherein said area of skin is on a leg of the human.

41. The method of claim 37, wherein said area of skin is on an arm of the human.

42. The method of claim 37, wherein said area of skin is in an armpit of the human.

43. The method of claim 37, wherein said area of skin is on the torso of the human.

44. The method of claim 1, wherein the composition is applied to an area of skin of a woman with hirsutism.

45. The method of claim 1, wherein said hair growth comprises androgen stimulated hair growth.

46. The method of claim 1, wherein the composition further includes a second component that also causes a reduction in hair growth.

47. The method of claim 1, wherein the inhibitor acts on telomerase.

48. The method of claim 1, wherein the inhibitor acts on a substrate targeted by telomerase.

49. The method of claim 1, wherein the composition is applied at least once a day over at least two days.

50. The method of claim 1, wherein said inhibitor is not a nucleoside analogue.

51. The method of claim 1, wherein said inhibitor is not AZT.

52. A method of reducing mammalian hair growth which comprises selecting an area of skin on a mammal from which reduced hair growth is desired; and applying to said area of skin a dermatologically acceptable non-depilatory composition comprising an inhibitor of telomerase in an amount effective to reduce hair growth.

* * * * *

UNITED STATES PATENT AND TRADEMARK OFFICE
CERTIFICATE OF CORRECTION

| | | |
|---|---|---|
| PATENT NO. | : 7,439,271 B2 | Page 1 of 1 |
| APPLICATION NO. | : 09/893252 | |
| DATED | : October 21, 2008 | |
| INVENTOR(S) | : Gurpreet S. Ahluwalia and Peter Styczynski | |

It is certified that error appears in the above-identified patent and that said Letters Patent is hereby corrected as shown below:

On the cover page, under item (56) References Cited, FOREIGN PATENT DOCUMENTS, "JP 9-113096" should be --JP 9-143096--

Col. 12, in claim 12, delete "(TTAGGG)3." and insert --(TTAGGG)$^3$ (SEQ ID NO:1).--

Col. 12, in claim 15, delete "C." and insert --C (SEQ ID NO:2).--

Signed and Sealed this

Sixth Day of January, 2009

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,439,271 B2 | Page 1 of 1 |
| APPLICATION NO. | : 09/893252 | |
| DATED | : October 21, 2008 | |
| INVENTOR(S) | : Gurpreet S. Ahluwalia and Peter Styczynski | |

It is certified that error appears in the above-identified patent and that said Letters Patent is hereby corrected as shown below:

On the cover page, under item (56) References Cited, FOREIGN PATENT DOCUMENTS, "JP 9-113096" should be --JP 9-143096--

Col. 9, in claim 12, line 45, delete "(TTAGGG)3." and insert --(TTAGGG)$^3$ (SEQ ID NO:1).--

Col. 9, in claim 15, line 54, delete "C." and insert --C (SEQ ID NO:2).--

This certificate supersedes the Certificate of Correction issued January 6, 2009.

Signed and Sealed this

Third Day of February, 2009

JOHN DOLL
*Acting Director of the United States Patent and Trademark Office*